US012698281B2

(12) United States Patent
Bassaganya-Riera

(10) Patent No.: US 12,698,281 B2
(45) Date of Patent: Aug. 4, 2026

(54) THIAZOLE DERIVATIVES FOR THERAPEUTIC USE

(71) Applicant: NIMML Institute, Blacksburg, VA (US)

(72) Inventor: Josep Bassaganya-Riera, Blacksburg, VA (US)

( * ) Notice: Subject to any disclaimer, the term of this patent is extended or adjusted under 35 U.S.C. 154(b) by 382 days.

(21) Appl. No.: 18/235,949

(22) Filed: Aug. 21, 2023

(65) Prior Publication Data

US 2024/0076296 A1 Mar. 7, 2024

Related U.S. Application Data

(60) Provisional application No. 63/371,992, filed on Aug. 19, 2022.

(51) Int. Cl.
| | |
|---|---|
| *C07D 417/14* | (2006.01) |
| *A61P 1/04* | (2006.01) |
| *A61P 37/06* | (2006.01) |
| *C07D 487/04* | (2006.01) |

(52) U.S. Cl.
CPC .............. *C07D 417/14* (2013.01); *A61P 1/04* (2018.01); *A61P 37/06* (2018.01); *C07D 487/04* (2013.01)

(58) Field of Classification Search
CPC ............................ C07D 417/14; C07D 487/04
See application file for complete search history.

(56) References Cited

FOREIGN PATENT DOCUMENTS

| WO | 2011079772 A1 | 7/2011 |
|---|---|---|
| WO | PCTUS2372536 | 1/2024 |

OTHER PUBLICATIONS

CA Reg. No. 2782689-90-9, entered into STN on Jul. 1, 2022, p. 1 (Year: 2022).*
Bright et al, Food Allergies: Diagnosis, Treatment and Prevention, 2023, Am Fam Physician, vol. 108, No. 2, p. 159-165 (Year: 2023).*
Autoimmune Disease, retrieved from https://larkinhealth.com/en/treatments-services/rheumatology/autoimmune-disease/ on Dec. 4, 2025 (Year: 2025).*
National Library of Medicine, Cyclohexyl(thiophen-2-yl)methanone, Pubchem CID 251194, Mar. 26, 2005, pp. 1-10.
National Library of Medicine, Phenyl-(5-phenylthiophen-2-yl)methanone, Pubchem CID 313817, Mar. 26, 2005, pp. 1-12.

* cited by examiner

*Primary Examiner* — Adam C Milligan
*Assistant Examiner* — Karen Cheng
(74) *Attorney, Agent, or Firm* — Elie Gendloff; Gendloff IP, LLC

(57) ABSTRACT

Provided are thiazole derivative compounds that can reduce CD4+ IFNγ+ T cells and inhibit or reduce inflammation. Also provided are methods of treating diseases characterized by gastrointestinal tract inflammation using the compounds.

5 Claims, 13 Drawing Sheets

| ID | Structure | Affinity (kcal/mol) |
|----|-----------|---------------------|
| 1 | | -7.2 |
| 2 | | -7.1 |
| 3 | | -6.9 |
| 4 | | -7.5 |
| 5 | | -7.3 |
| 6 | | -7.3 |
| 7 | | -7.3 |
| 8 | | -7.4 |

FIG. 1A

| ID | Structure | Affinity (kcal/mol) |
|---|---|---|
| 9 | | -7.5 |
| 10 | | -7.4 |
| 11 | | -7.8 |
| 12 | | -7.1 |
| 13 | | -6.9 |
| 14 | | -7 |
| 15 | | -7.4 |
| 16 | | -7.3 |

FIG. 1B

| ID | Structure | Affinity (kcal/mol) |
|----|-----------|---------------------|
| 17 | | -7.7 |
| 18 | | -6.9 |
| 19 | | -7.5 |
| 20 | | -7.3 |
| 21 | | -7.3 |
| 22 | | -8.1 |
| 23 | | -7.6 |
| 24 | | -7.6 |

FIG. 1C

| ID | Structure | Affinity (kcal/mol) |
|---|---|---|
| 25 | | -7.2 |
| 26 | | -7.1 |
| 27 | | -6.8 |
| 28 | | -8.3 |
| 29 | | -7.9 |
| 30 | | -7.1 |
| 31 | | -7.6 |
| 32 | | -7.4 |

FIG. 1D

| ID | Structure | Affinity (kcal/mol) |
|---|---|---|
| 33 | | -7.6 |
| 34 | | -7.3 |
| 35 | | -7.6 |
| 36 | | -8.1 |
| 37 | | -7.7 |
| 38 | | -7.6 |
| 39 | | -6.7 |
| 40 | | -7 |

FIG. 1E

| ID | Structure | Affinity (kcal/mol) |
|----|-----------|---------------------|
| 41 | | -6.9 |
| 42 | | -7.6 |
| 43 | | -7.3 |
| 44 | | -7.6 |
| 45 | | -7.2 |
| 46 | | -7.8 |
| 47 | | -7.7 |
| 48 | | -7.5 |

FIG. 1F

| ID | Structure | Affinity (kcal/mol) |
|---|---|---|
| 49 | | -7.6 |
| 50 | | -7.7 |
| 51 | | -8.2 |
| 52 | | -7.6 |
| 53 | | -7.7 |
| 54 | | -7 |
| 55 | | -6.9 |
| 56 | | -6.6 |

FIG. 1

| ID | Structure | Affinity (kcal/mol) |
|----|-----------|---------------------|
| 57 | | -8.2 |
| 58 | | -7 |
| 59 | | -7.6 |
| 60 | | -8 |
| 61 | | -8.1 |
| 62 | | -8 |
| 63 | | -7.6 |
| 64 | | -7.4 |

FIG. 1G

| ID | Structure | Affinity (kcal/mol) |
|----|-----------|---------------------|
| 65 | | -7.7 |
| 66 | | -7.9 |
| 67 | | -7.5 |
| 68 | | -8.7 |
| 69 | | -8.2 |

Colon Score

CD4+ IFNy+

THIAZOLE DERIVATIVES FOR THERAPEUTIC USE

CROSS-REFERENCE TO RELATED APPLICATIONS

This application claims the benefit of U.S. Provisional Application No. 63/371,992, filed Aug. 19, 2022, and incorporated by reference herein in its entirety.

BACKGROUND OF THE INVENTION

(1) Field of the Invention

The present invention relates to the field of medical treatments for diseases and disorders. More specifically, the present invention relates to classes of biologically active compounds that treat or prevent inflammatory and immune-mediated diseases primarily those of the gastrointestinal tract caused by food antigens, infectious agents, autoimmunity, or radiation, such as Celiac disease, Clostridioides difficile infection, viral infections, Crohn's disease, ulcerative colitis, radiation mucositis, and radiation enteritis.

(2) Description of the Related Art

Dysregulation of the immune system can result in numerous health conditions and disorders including food allergies, complications arising from bacterial or viral infections, autoimmune diseases, and chronic, unresolved inflammation. Current strategies to treat these conditions include the use of corticosteroids, the amelioration of symptoms or inhibiting key pathways tied to immune activation. Often, these strategies result in a loss of response over time or are poorly tolerated with many side effects tied to broad immunosuppression. New strategies have the potential to reach millions of patients.

IL-18 is a proinflammatory cytokine from the IL-1 super-family associated with IFNγ production, inflammasome function and NF-κB activation. Through binding to a dimeric receptor complex, IL-18Rα and IL-18Rβ, IL-18 drives IFNγ production from CD4+ T helper 1 cells and inflammatory polarization of macrophages. The pathway has a natural feedback loop through and extracellular factor, IL-18BP, which has the potential to sequester IL-18. Additionally, IL-18 competes with IL-37 for the same receptor subunit. Epithelial cells from the lung, skin and gastrointestinal tract are the predominant producers of IL-18. Recent genetic studies have associated polymorphisms and mutations in IL-18 or its promoter region to arthritis, lupus, and inflammatory bowel disease.

BRIEF SUMMARY OF THE INVENTION

Provided is a compound comprising Formula I, its stereoisomers or a pharmaceutically acceptable salt or ester thereof, Formula I wherein $A^1$, $A^2$, $A^3$ and $A^7$ are each independently C or N;

$A^4$ is C or O;

$A^5$ is C or N;

$A^6$ is S, N or O; and $R^1$, $R^2$, $R^3$, $R^4$, $R^5$, $R^6$, and $R^7$ are each independently hydrogen, hydroxy, carboxyl, acetyl, halo, a substituted or unsubstituted alkane, alkene, alkyne, amino, alkyl, alkoxy, carboxyalkyl, alkylamide, acyl, acylamino aryl, arylalkyl, heteroalkyl, heteroalkoxy, heterocarboxyalkyl, heteroacyl, heteroacylamino, heteroaryl, or heteroarylalkyl; or a substituted or unsubstituted five-membered heterocycle where any member of the given ring may be C, N, O or S.

Also provided is a method of preventing or treating a disease characterized by excess CD4+ IFNγ+ cells in a patient. The method comprises administering the above compound to the patient in a manner sufficient to prevent or treat the disease.

BRIEF DESCRIPTION OF THE SEVERAL VIEWS OF THE DRAWINGS

Figure 1A:
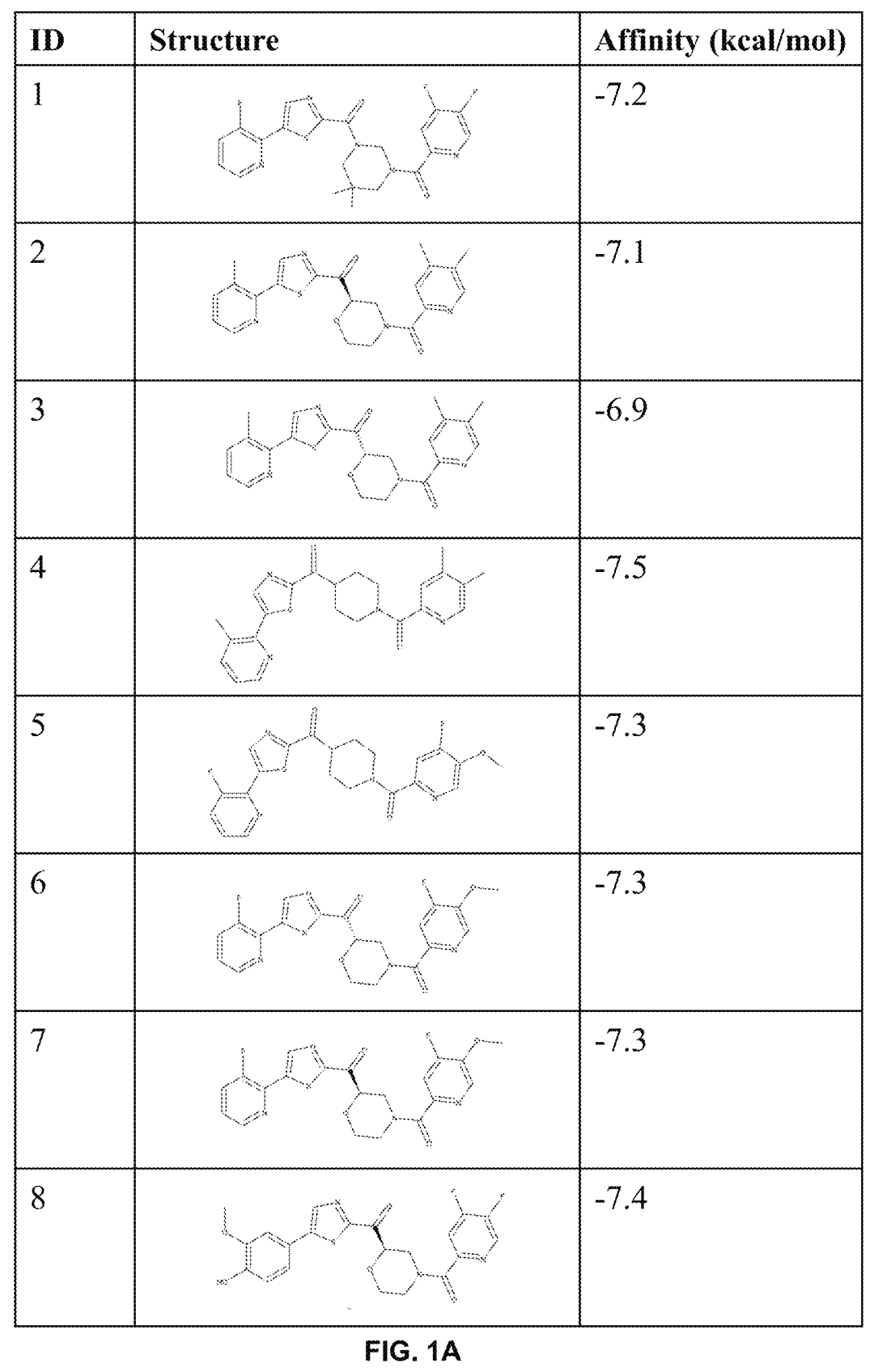
Figure 1B:
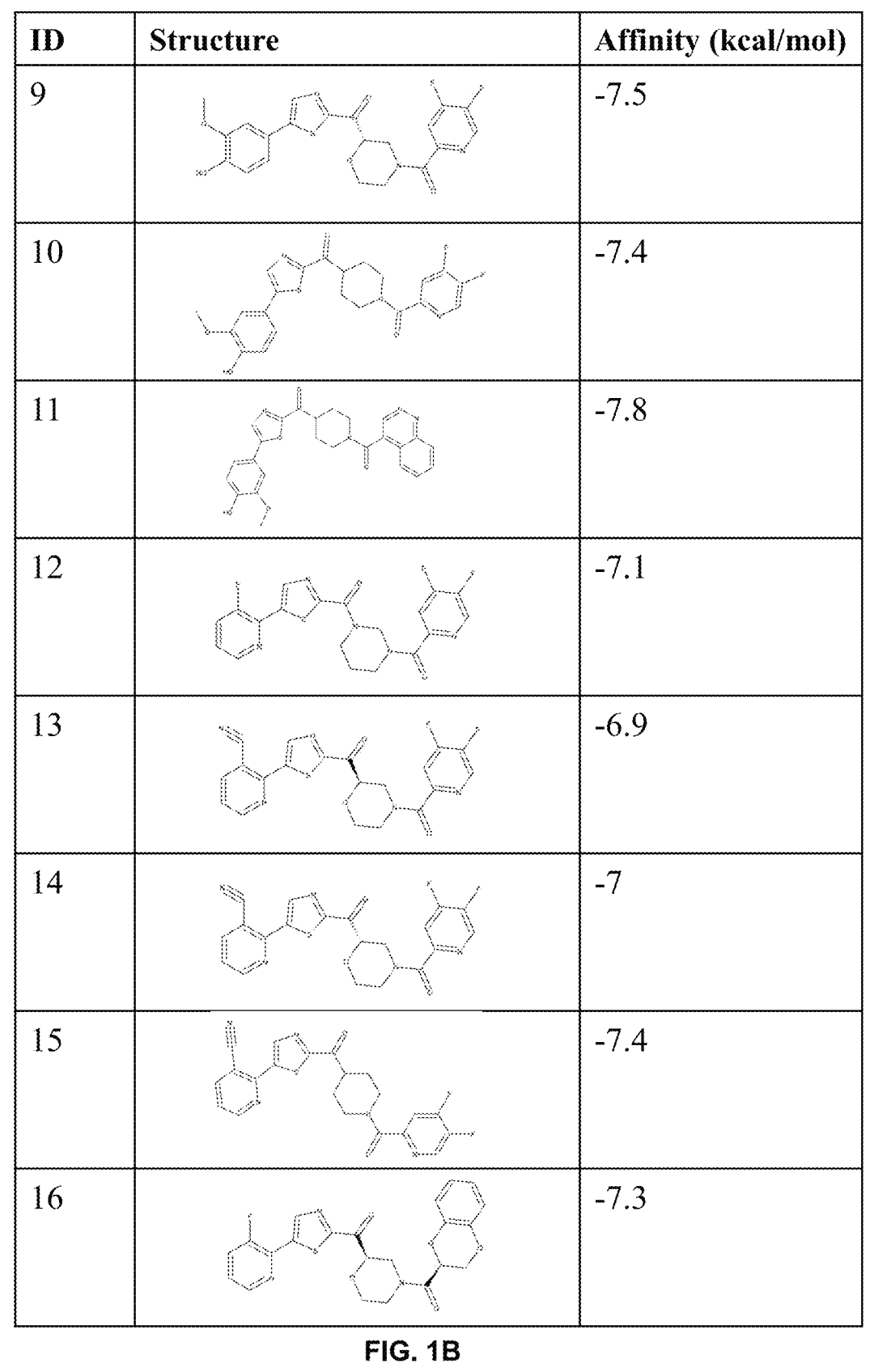
Figure 1C:
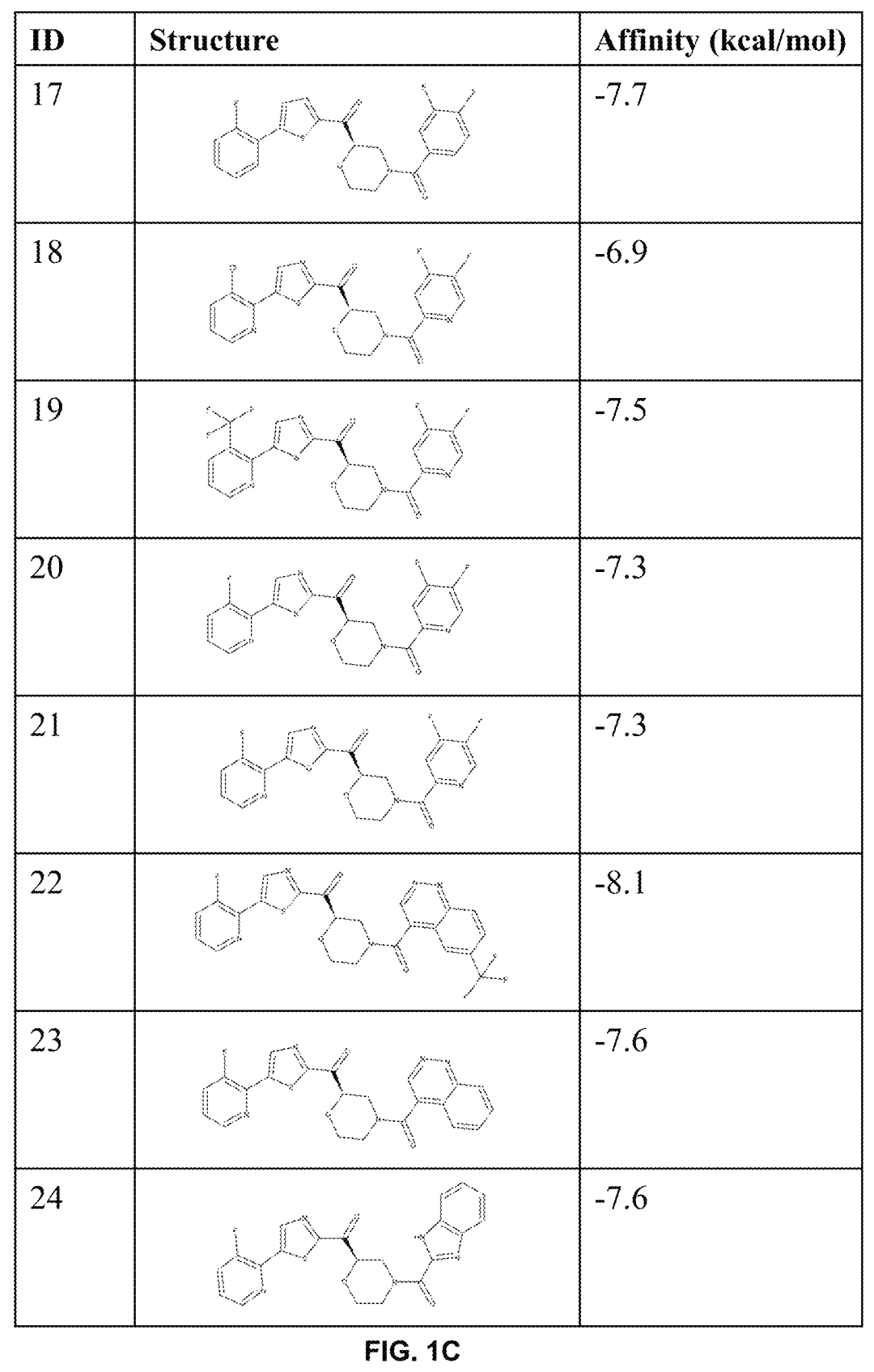
Figure 1D:
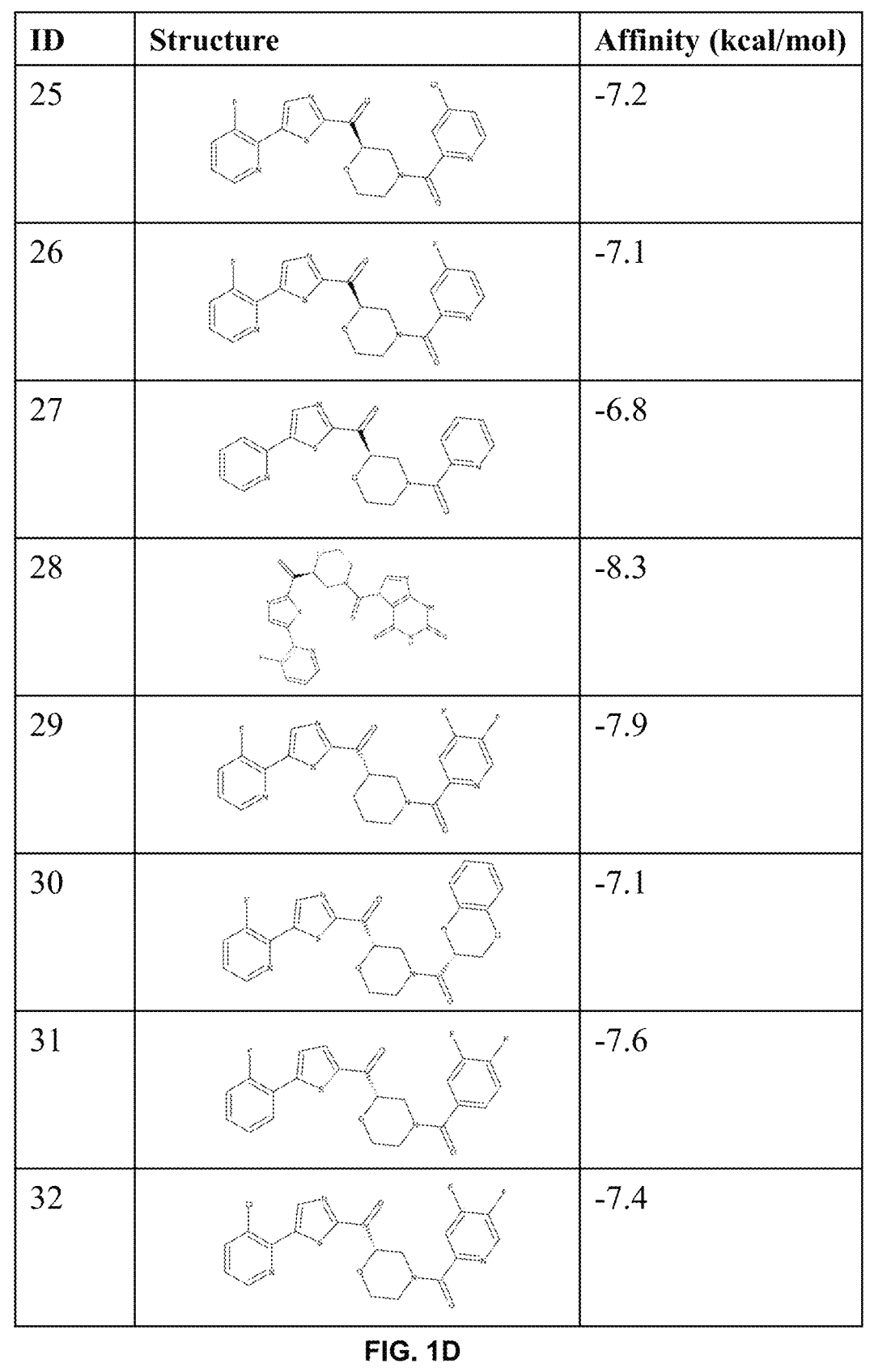
Figure 1E:
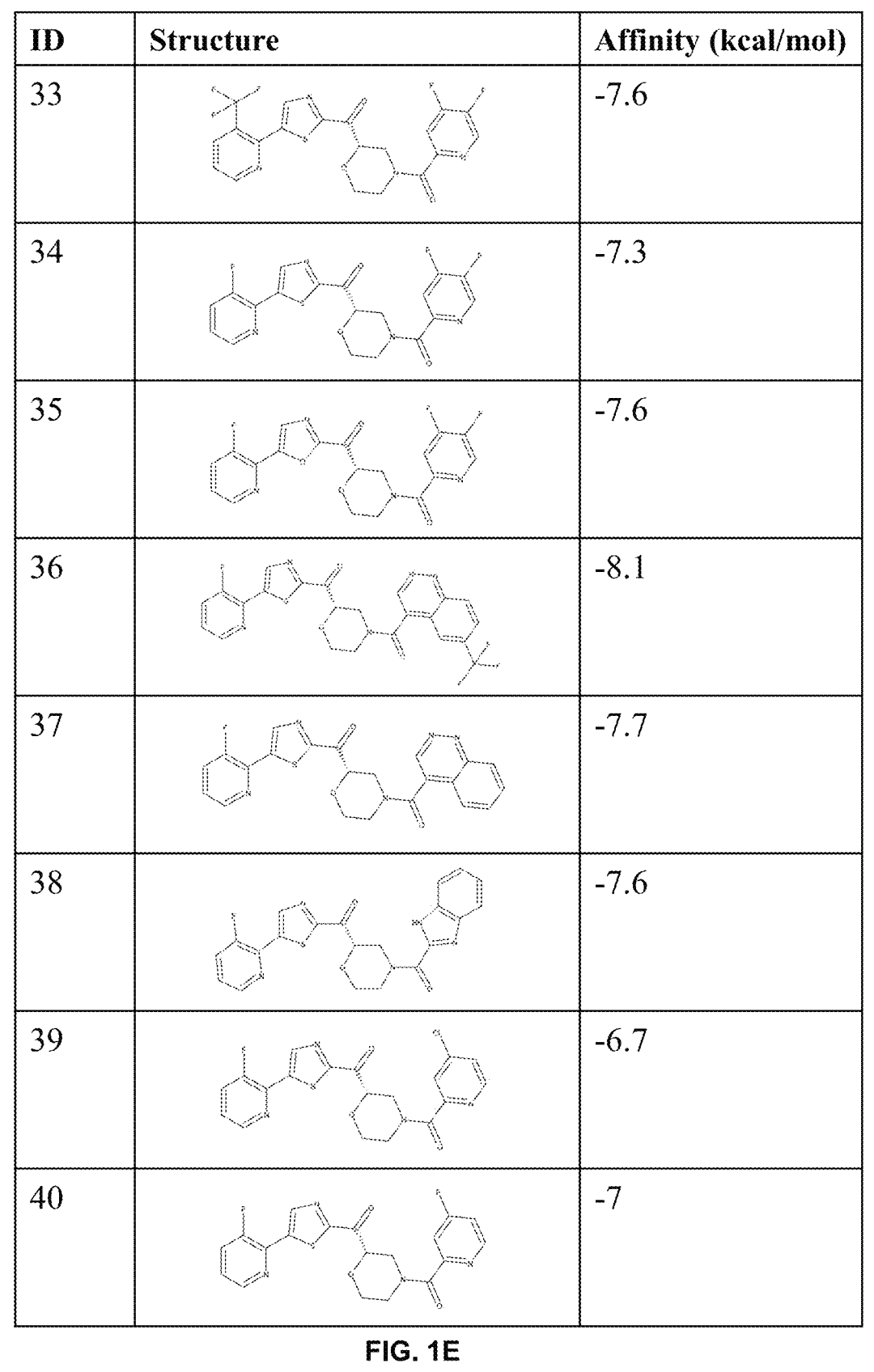
Figure 1F:
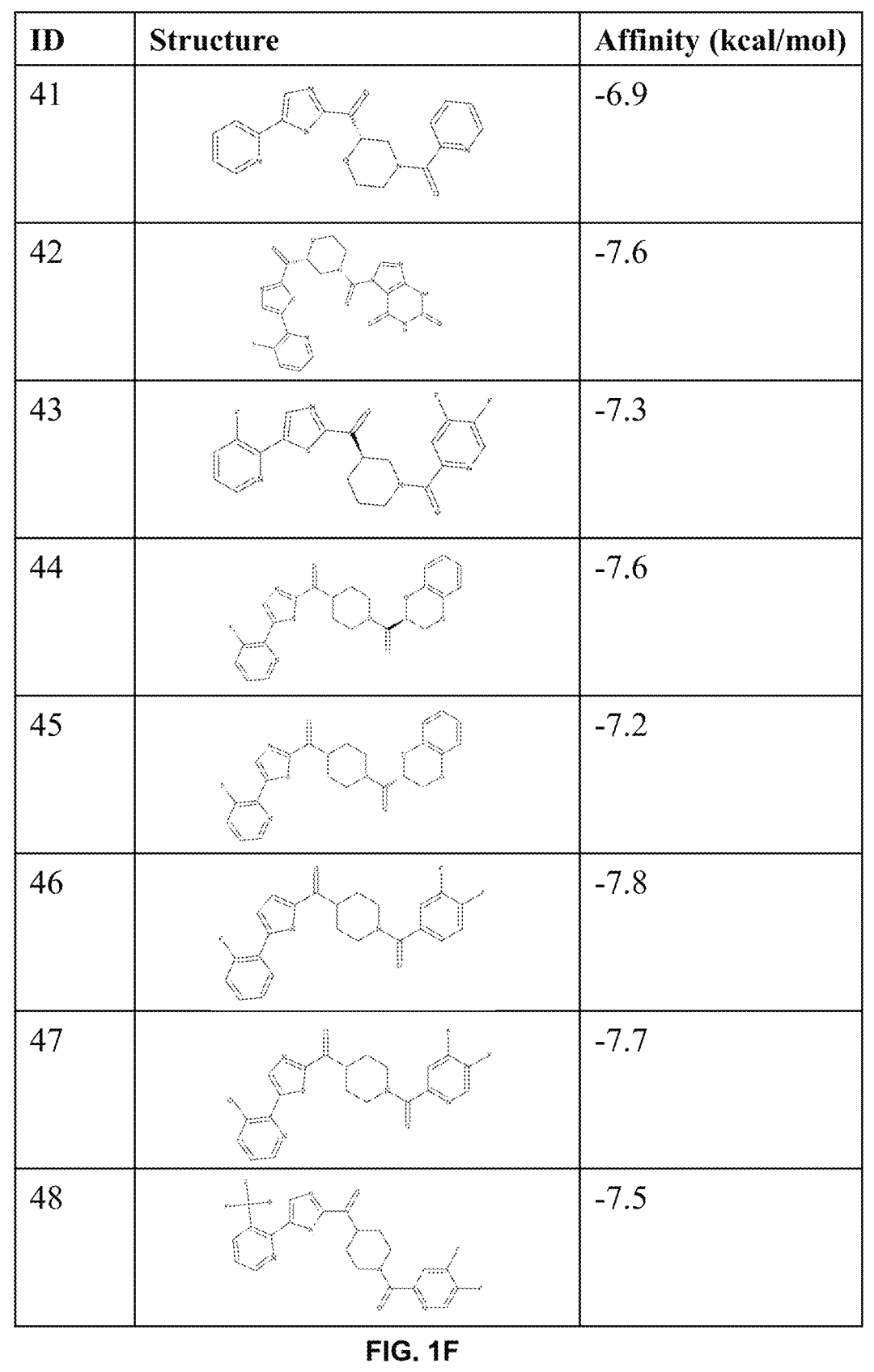
Figure 1:
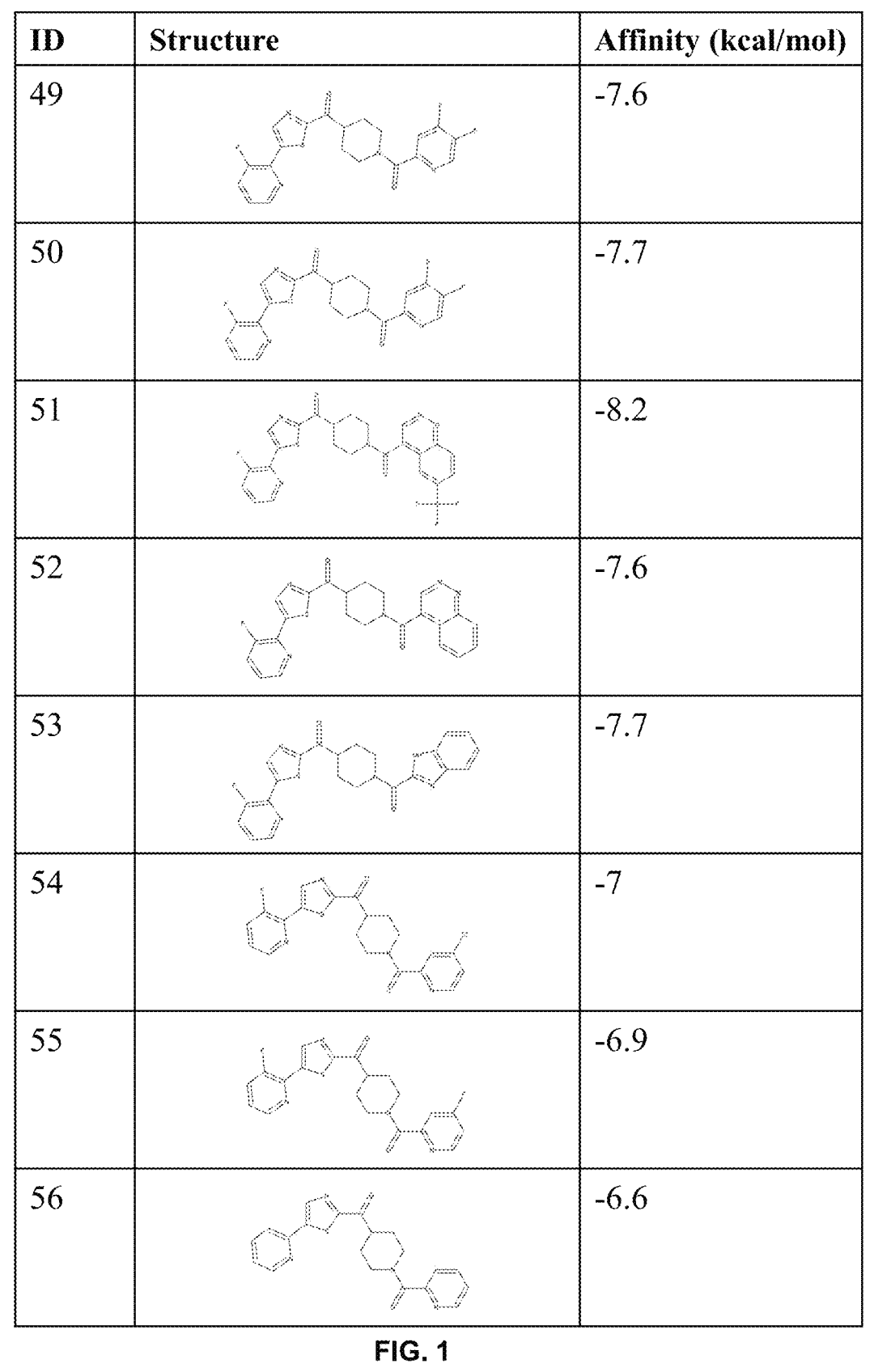
Figure 1G:
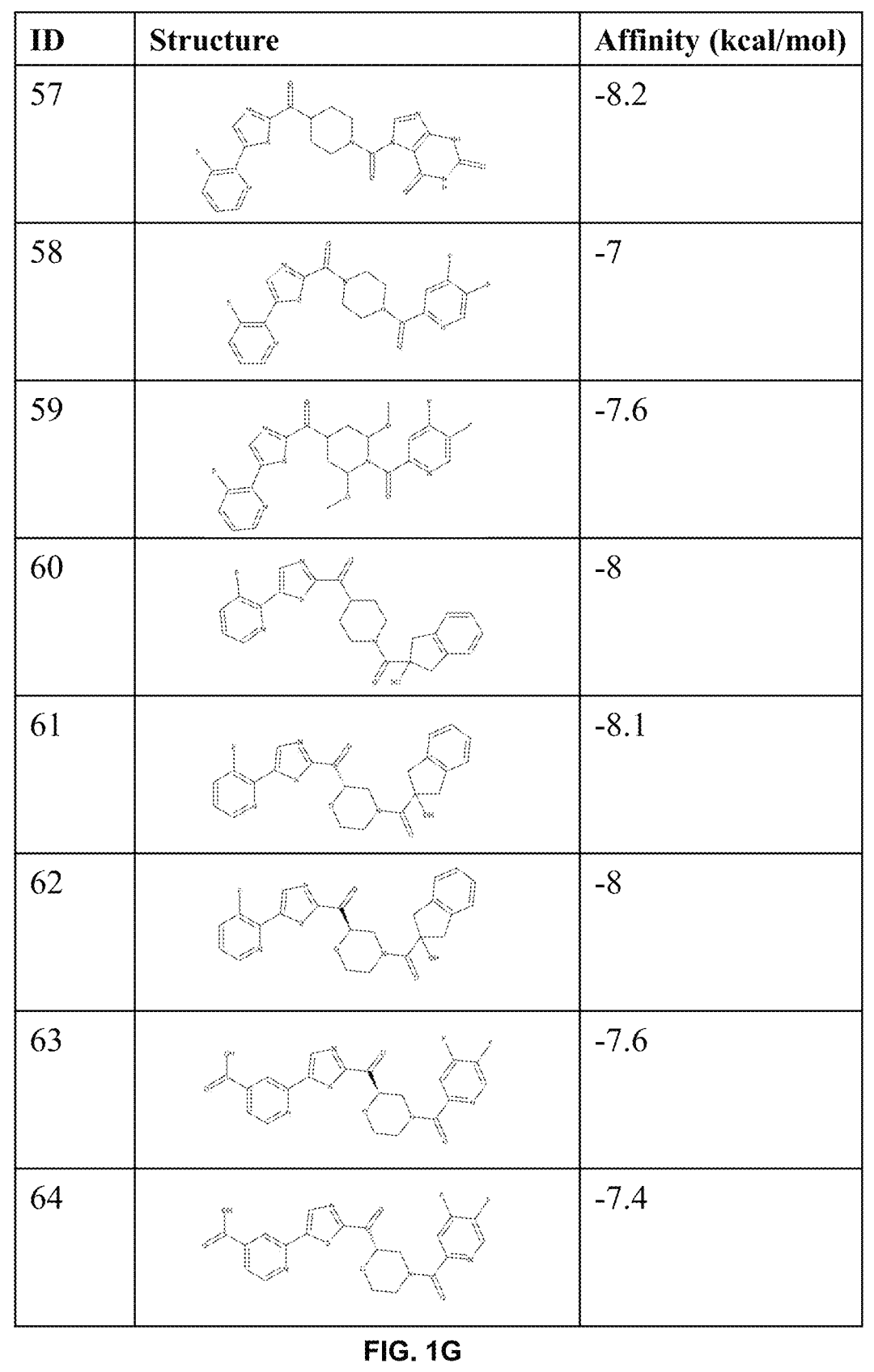
Figure 1H:
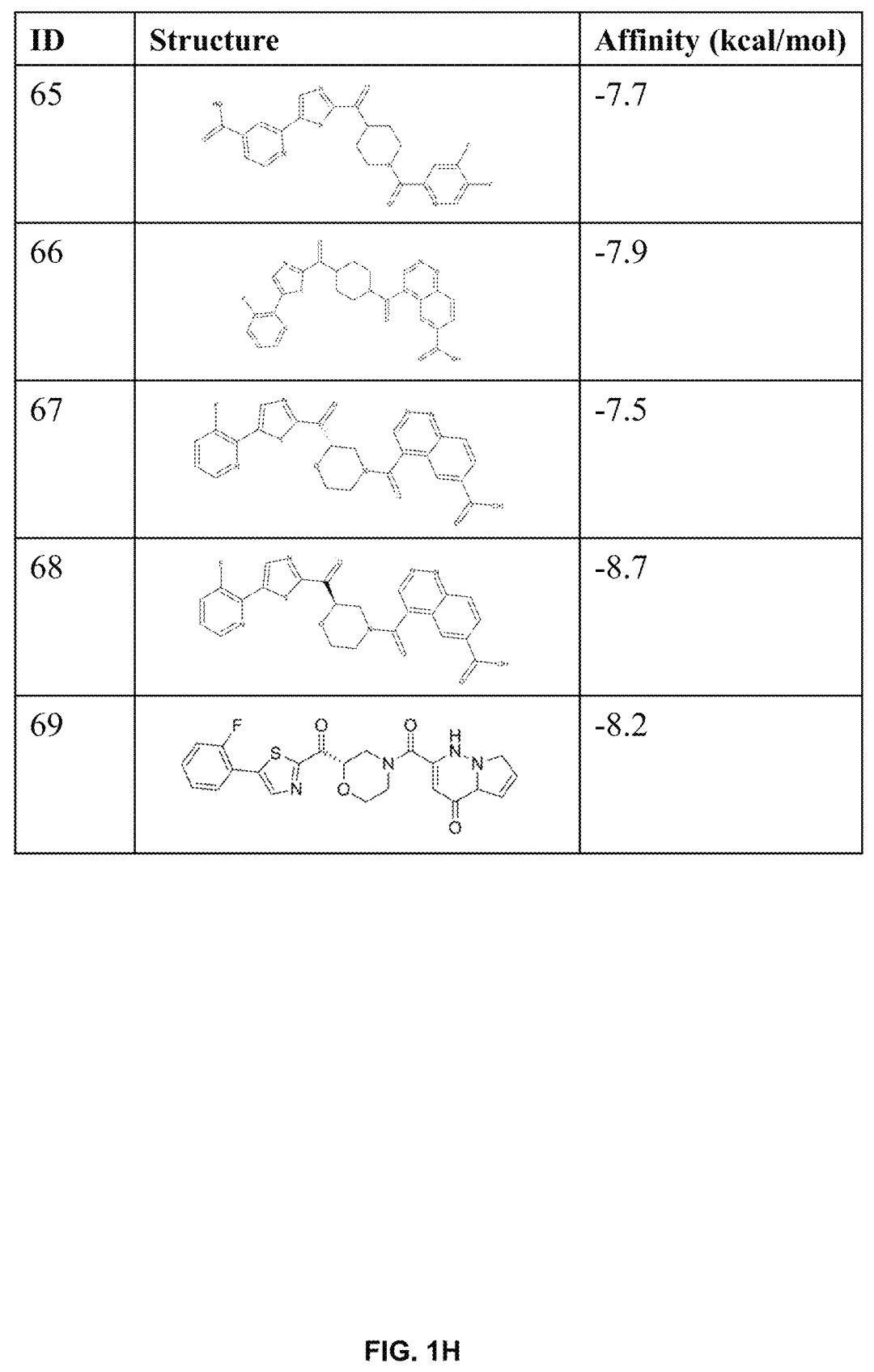

FIGS. 1 and 1A-1H show the structures of Compounds 1-69, with a computational prediction of binding of those compounds to the complex of IL-18 with binding partners and receptors.

FIGS. 2A-2H show exemplary compounds of the invention: Compound 11 (FIG. 2A); Compound 20 (FIG. 2B); Compound 34 (FIG. 2C); Compound 40 (FIG. 2D); Compound 37 (FIG. 2E); Compound 42 (FIG. 2F); Compound 52 (FIG. 2G); and C68 (FIG. 2H).

DETAILED DESCRIPTION OF THE INVENTION

Figure 3:
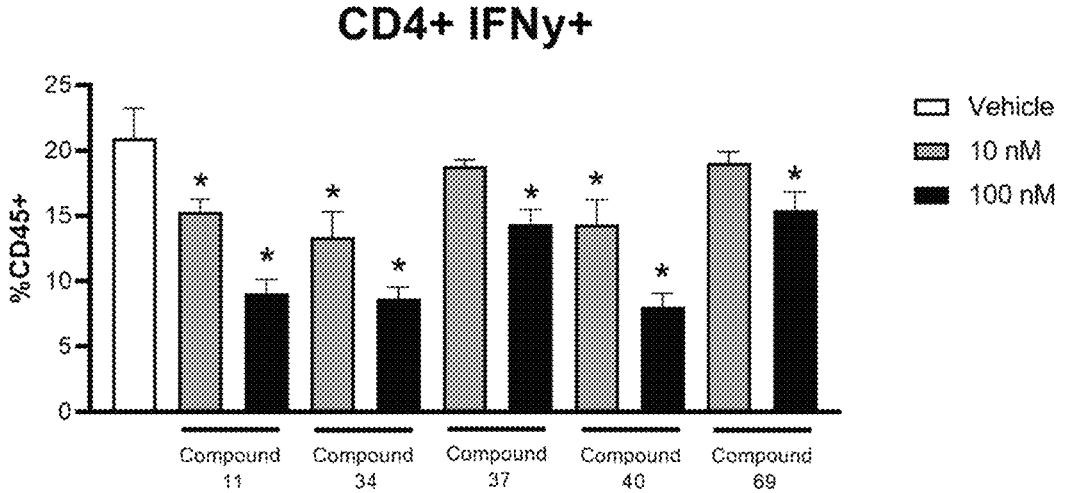
FIG. 3 is a graph providing experimental validation of the immune effects of five exemplary compounds in CD4+ T cells in vitro. Measurements were of CD4+ IFNγ+ cells by flow cytometry. Statistical significance (P<0.05) is marked by asterisks.

The present invention provides compounds that have been developed by novel medicinal chemistry approaches, screened using in silico and in vitro approaches, and validated to be biologically active in in vivo models of disease. Therapeutic use of these compound may result in an induction or maintenance of beneficial responses in various disease conditions, including but not limited to infectious diseases caused by Clostridioides difficile, Escherichia coli, Campylobacter jejuni, Salmonella, Mycobacterium tuberculosis, Norovirus, Rotavirus, Cytomegalovirus, or Entamoeba histolytica, radiation mucositis, radiation enteritis, or radiation colitis, Celiac disease, atopic dermatitis or other food-antigen related disease, and autoimmune or inflammatory disease selected from ankylosing spondylitis, Crohn's disease, eosinophilic esophagitis, systemic scleroderma, psoriasis, or ulcerative colitis.

In some embodiments, a compound is provided comprising Formula I, its stereoisomers or a pharmaceutically acceptable salt or ester thereof, Formula I wherein $A^1$, $A^2$, $A^3$ and $A^7$ are each independently C or N;

$A^4$ is C or O;

$A^5$ is C or N;

$A^6$ is S, N or O; and $R^1$, $R^2$, $R^3$, $R^4$, $R^5$, $R^6$, and $R^7$ are each independently hydrogen, hydroxy, carboxyl, acetyl, halo, a substituted or unsubstituted alkane, alkene, alkyne, amino, alkyl, alkoxy, carboxyalkyl, alkylamide, acyl, acylamino aryl, arylalkyl, heteroalkyl, heteroalkoxy, heterocarboxyalkyl, heteroacyl, heteroacylamino, heteroaryl, or heteroarylalkyl; or a substituted or unsubstituted five-membered heterocycle where any member of the given ring may be C, N, O or S.

In some embodiments, $R^1$, $R^2$, $R^3$, $R^4$ and $R^5$ are each independently hydrogen, hydroxy, carboxyl, halo, a substituted or unsubstituted alkane, alkene, alkyne, alkyl, or alkoxy. In some of these embodiments, $R^1$, $R^2$, $R^3$, $R^4$ and $R^5$ are each independently hydrogen, hydroxy, fluorine, chlorine, methyl, carboxyl, In various embodiments, either $R^6$ or $R^7$ is hydrogen and the other of $R^6$ or $R^7$ is wherein $R^8$ is hydrogen, hydroxy, acetyl, halo, carboxyl; a substituted or unsubstituted amino, alkyl, alkoxy, carboxyalkyl, alkylamide, acyl, acylamino aryl, arylalkyl, heteroalkyl, heteroalkoxy, heterocarboxyalkyl, heteroacyl, heteroacylamino, heteroaryl, or heteroarylalkyl; or a substituted or unsubstituted five-membered heterocycle where any member of the given ring may be C, N, O, or S. In some of these embodiments, $R^8$ comprises an aromatic ring. In additional embodiments, $R^8$ is a substituted or unsubstituted arylalkyl, heteroaryl, or heteroarylalkyl, optionally including a five- or six-membered heterocycle where any member of the given ring may be C, N, O, or S. In exemplary embodiments, wherein $R^8$ is In specific embodiments, the compound is any one of compounds 1-69 of FIGS. 1A-1H. In some of these embodiments, the compound is any one of compounds 6, 7, 11, 20, 34, 37, 40, 42, 52, 55, 58, 68 or 69 of FIGS. 1A-1H.

As demonstrated in the examples below, the above compounds can reduce CD4+ IFNγ+ cells in a CD4+ T cell culture. The examples also show that the compounds can inhibit or reduce inflammation of a gastrointestinal tract. As such, the compounds of the present invention can prevent or treat diseases characterized by gastrointestinal tract inflammation such as colitis or enteritis, for example colitis or enteritis caused by an infectious agent such as Clostridioides difficile, Escherichia coli, Campylobacter jejuni, Salmonella, Mycobacterium tuberculosis, Norovirus, Rotavirus, Cytomegalovirus, or Entamoeba histolytica, or radiation mucositis, radiation enteritis, or radiation colitis.

Other diseases characterized by inflammation of the gastrointestinal tract that can be prevented or treated with the invention compounds are food-antigen related diseases such as celiac disease or atopic dermatitis.

Additional inflammatory diseases that can be prevented or treated by the above compounds are autoimmune diseases and inflammatory diseases such as ankylosing spondylitis, Crohn's disease, eosinophilic esophagitis, systemic scleroderma, psoriasis, or ulcerative colitis.

Any of these compounds can be prepared by the skilled artisan without undue experimentation, e.g., by using the methods described in Example 2, or similar methods.

The compound of Formula 1 can be formulated in any compatible excipient, alone or in combination with any other compound, e.g., another pharmaceutically active compound, for example another compound of Formula 1.

Some embodiments of the present invention relate to the use of the above-mentioned compounds comprising Formula 1 formulated in compositions, including pharmaceutical compositions, that comprise at least one of the compounds of the invention in a pharmaceutically acceptable excipient. In some of these embodiments, the compound is suitable for administration to a patient by any parenteral, enteral, transmucosal, or transdermal route which effectively transports the compound of interest to the appropriate or desired site of action, such as oral, nasal, topical, pulmonary, transdermal or parenteral, e. g., rectal, subcutaneous, intravenous, intraurethral, intramuscular, intranasal, ophthalmic solution or an ointment. The preparation of these formulations are within the skill of the art; methods for preparing formulations are provided, for example in Remington's Pharmaceutical Sciences (A. R. Gennaro, Ed.), 20th edition, Williams & Wilkins PA, USA (2000).

In some of these embodiments, the compound is combined with at least another active compound, e.g., another compound effective in preventing or treating a disease, disorder or condition in a mammal. Alternatively or additionally, the compositions can be formulated with at least one inert ingredient as a carrier or excipient such as: cosolvents, surfactants, oils, humectants, emollients, preservatives, stabilizers and antioxidants. Any pharmacologically acceptable buffer may be used, e. g., TRIS or phosphate buffers.

Typical compositions include the compounds of the invention, or derivatives thereof, associated with pharmaceutically acceptable excipients, which may be a carrier or a diluent, by way of example. Such compositions can be in the form of a capsule, sachet, paper or other container. In making the compositions, conventional techniques for the preparation of pharmaceutical compositions may be used. For example, the compound of interest can be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compound of interest can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

For nasal administration, the preparation may contain the compound of interest dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical formulations, the compound of interest is placed in a dermatological vehicle as is known in the art. The amount of the compound of interest to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of interest and selects the amount of formulation administered, depending upon clinical experience with the patient in question or with similar patients.

For ophthalmic applications, the compound of interest is formulated into solutions, suspensions, and ointments appropriate for use in the eye. For rectal applications, the compound of interest is formulated into solutions and suspensions appropriate for delivery by enema.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the compound of interest with an inert pharmaceutical diluent and filling the mixture into a hard gelatin capsule of appropriate size. Soft gelatin capsules are prepared by machine encapsulation of slurry of the compound of interest with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e. g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill, such as the use of suitable injectable solutions or suspensions. The formulation, which is sterile, is suitable for various topical or parenteral routes including intra-dermal, intramuscular, intravascular, and subcutaneous.

In addition to the compound of interest, the compositions may include, depending on the formulation and mode of delivery desired, pharmaceutically acceptable, non-toxic carriers or diluents, which include vehicles commonly used to form pharmaceutical compositions for animal or human administration. The diluent is selected so as not to unduly affect the biological activity of the combination.

Examples of such diluents that are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, additives can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives, and excipients are those amounts that are effective to obtain a pharmaceutically acceptable formulation in terms of solubility, biological activity, etc.

The compound of interest may be incorporated into a microsphere. The compound of interest can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stifling to produce water in oil emulsion. Glutaraldehyde solution is then added to the emulsion and the emulsion stirred to cross-link the albumin. The microspheres can then be isolated by centrifugation, the oil removed and the spheres washed, e. g., with petroleum ether followed by ethanol. Finally, the microspheres can be sieved and collected and dried by filtration.

Starch microspheres can be prepared by adding a warm aqueous starch solution, e. g. of potato starch, to a heated solution of polyethylene glycol in water with stifling to form an emulsion. When the two-phase system has formed (with the starch solution as the inner phase) the mixture is then cooled to room temperature under continued stifling whereupon the inner phase is converted into gel particles. These particles are then filtered off at room temperature and slurred in a solvent such as ethanol, after which the particles are again filtered off and laid to dry in air. The microspheres can be hardened by well-known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form Schiff bases with amino groups. Epichlorohydrin activates compounds with nucleophiles such as amino or hydroxyl to an epoxide derivative.

Another embodiment of the invention is the dosage scheme. The term "unit dosage form" refers to physically discrete units suitable as unitary dosages for subjects, e. g., mammalian subjects, e. g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions can be included in kits, which can contain one or more unit dosage forms of the composition and instructions for use to treat one or more of the disorders described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long-term source of therapeutic compound. Such slow-release systems are applicable to formulations for delivery via topical, intraocular, oral, and parenteral routes.

An effective amount of the compound of interest is employed in treatment. The dosage of compounds used in accordance with the invention varies depending on the compound and the disease, disorder or condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer. The skilled artisan can determine an appropriate dosage for any particular use of route of administration without undue experimentation.

The pharmaceutical compositions described above can be formulated for administration to any mammal, including but not limited to farm animals (e.g., cows, pigs, goats, sheep, llamas, alpacas, mink, etc.), domestic animals (e.g., dogs, cats, mice, rats, gerbils, guinea pigs, ferrets, etc) and humans.

Also provided herein are methods of treating mammals using the pharmaceutical compositions of Formula 1 described above, for preventing or treating a disease characterized by excess CD4+ IFNγ+ cells in a patient. The method comprises administering any of the above compounds to the patient in a manner sufficient to prevent or treat the disease.

The patient in these embodiments can be any mammal, including but not limited to farm animals (e.g., cows, pigs, goats, sheep, llamas, alpacas, mink, etc.), domestic animals (e.g., dogs, cats, mice, rats, gerbils, guinea pigs, ferrets, etc) and humans.

In some of these embodiments, the disease is colitis or enteritis, including but not limited to colitis or enteritis caused by an infectious agent selected from Clostridioides difficile, Escherichia coli, Campylobacter jejuni, Salmonella, Mycobacterium tuberculosis, Norovirus, Rotavirus, Cytomegalovirus, or Entamoeba histolytica.

In other embodiments, the infectious disease may be caused by viruses in the families adenoviridae, parvoviridae, poxviridae, hepadnaviridae, picornaviridae, coronaviridae, flaviviridae, retroviridae, orthomyxoviridae, paramyxoviridae, filoviridae, or reoviridae; bacteria in the genera Bacillus, Brucella, Bordetella, Chlamydia, Corynebacterium, Legionella, Pseudomonas, Staphylococcus, or Yersinia; or fungi in the genera Aspergillus, Candida, or Cryptococcus.

In other embodiments, the disease is radiation-induced inflammation of the gastrointestinal tract including but not limited to radiation mucositis, radiation enteritis, or radiation colitis.

In additional embodiments, the disease is a food-antigen related disease, for example celiac disease or atopic dermatitis.

In further embodiments, the disease is an autoimmune disease or inflammatory disease. Nonlimiting examples include metabolic syndrome, obesity, prediabetes, cardiovascular disease, type 2 diabetes, nonalcoholic steatohepatitis, nonalcoholic fatty liver disease, cirrhosis, asthma, chronic granulomatous disease, graft versus host disease, tumor necrosis factor receptor associated periodic syndrome, muscle wasting, acute colonic diverticulitis, chronic obstructive pulmonary disease, idiopathic pulmonary fibrosis, Alzheimer's disease, Parkinson's disease, stroke, traumatic brain injury, irritable bowel syndrome, lupus, rheumatoid arthritis, osteoarthritis, Sjogren's syndrome, type 1 diabetes, multiple sclerosis, sarcoidosis, Guillain-Barre syndrome, Grave's disease, antiphospholipid syndrome, vasculitis, ankylosing spondylitis, Crohn's disease, eosinophilic esophagitis, systemic scleroderma, psoriasis, or ulcerative colitis.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Example 1

Molecular Docking

IL-18 is a proinflammatory cytokine of the IL-1 family associated with increasing production of interferon gamma. Potential ligands were docked into complexes of IL-18 and its binding partners and receptors.
Methods A grid space of the predicted binding pocket was defined. Three dimensional structures of the ligands with defined atomic charge were docked into the defined region. A binding affinity was calculated based on interactions between the ligand and protein structure. Potential ligands were analyzed and ranked by raw binding affinity, molecular weight normalized binding affinity and binding pose among other criteria.
Results Exemplary docked structures and resultant binding affinities are presented in FIGS. 1A-1H. Docked structures were identified to have binding affinities ranging from −6.6 kcal per mole to −8.7 kcal per mole. Structures with the most favorable binding affinity included compounds 22, 36, 68 and 69; all of which had binding affinities greater than 8.

Example 2

Synthesis of Compound 11

Figures 2A, 2B, 2C, 2D:
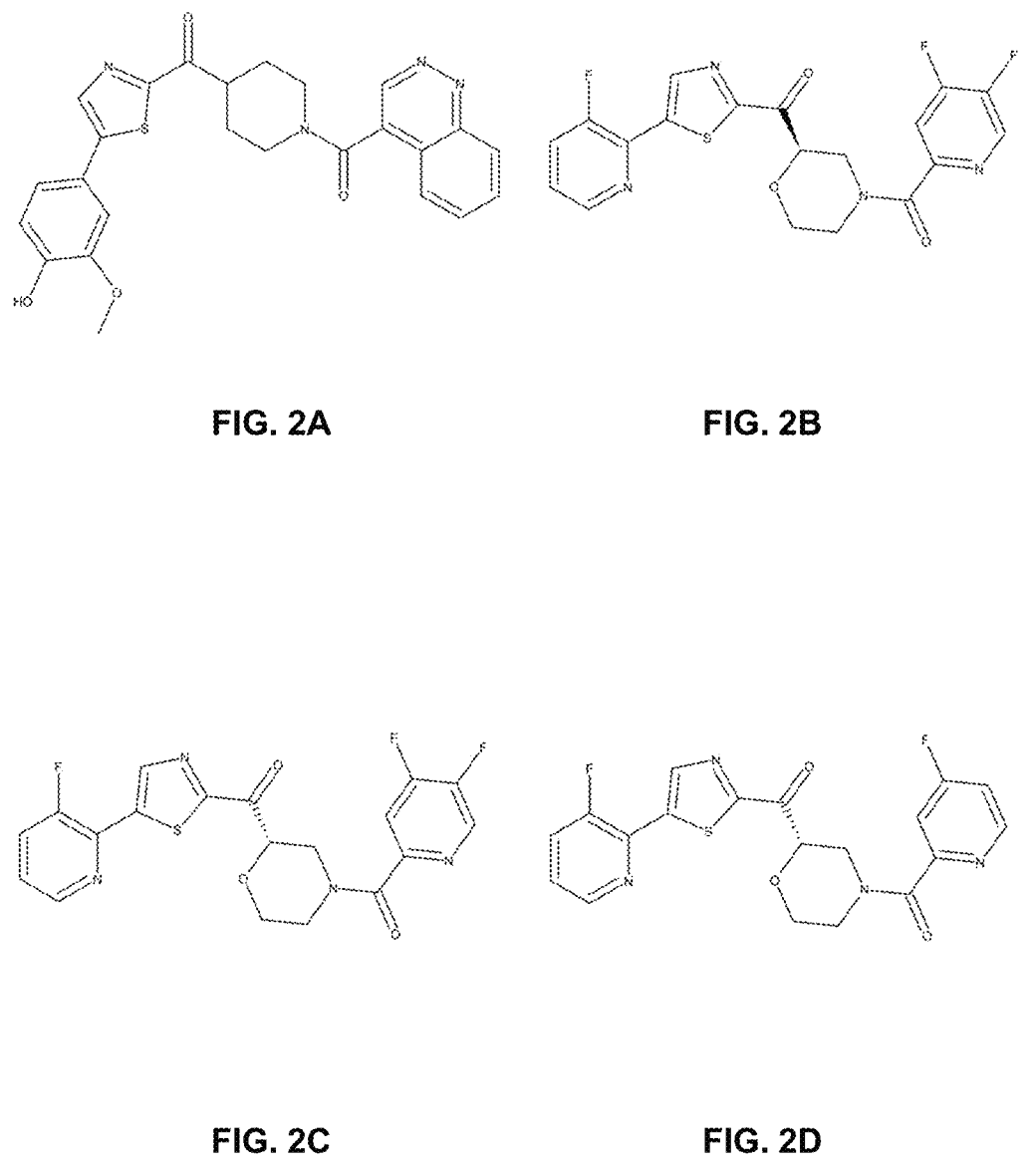

The synthesis of cinnolin-4-yl(4-(5-(4-hydroxy-3-methoxyphenyl)thiazole-2-carbonyl)-piperidin-1-yl)methanone (Compound 11 [FIG. 2A]) was a five-step process.

Carbonyldiimidazole was added to a solution of 1-(tert-butoxycarbonyl) piperidine-4-carboxylic acid in DCM. After 40 minutes, N,O-dimethylhydroxylamine hydrochloride was added to the reaction mixture. The reaction mixture was stirred at room temperature for 12 h. After completion of the reaction, the reaction mixture was diluted with cold water. Tert-butyl 4-(methoxy(methyl)carbamoyl)piperidine-1-carboxylate was isolated as product.

Potassium carbonate was added to a stirred solution of 2-methoxy-4-(4,4,5,5-tetramethyl-1,3,2-dioxaborolan-2-yl) phenol and methyl 5-bromothiazole in 1,4-dioxane-H2O. The reaction mixture was de-gassed with nitrogen after which tetrakis(triphenylphosphine)palladium(0) was added. The reaction mixture was stirred at 110° C. for 12 h. After completion of the reaction, the reaction mixture was diluted with water and extracted to afford 2-methoxy-4-(thiazol-5-yl) phenol as product.

N-butyllithium was added to a stirred solution of 2-methoxy-4-(thiazol-5-yl) phenol in dry THF over 10 minutes. After 40 minutes, tert-butyl 4-(methoxy(methyl)carbamoyl)piperidine-1-carboxylate dissolved in dry THF was added. The reaction mixture was stirred for 12 h. After completion of the reaction, the mixture was quenched in saturated ammonium chloride, extracted and dried to afford tert-butyl 4-(5-(4-hydroxy-3-methoxyphenyl)thiazole-2-carbonyl) piperidine-1-carboxylate as product.

Ether (2 M) in hydrochloric acid was added to a stirred solution of tert-butyl 4-(5-(4-hydroxy-3-methoxyphenyl) thiazole-2-carbonyl) piperidine-1-carboxylate in DCM. The reaction mixture was stirred at room temperature for 12 h. After completion of the reaction, solvent was distilled off to afford (5-(4-hydroxy-3-methoxyphenyl) thiazol-2-yl)(piperidin-4-yl)methanone hydrochloride as product.

Hydroxybenzotriazole, EDC-HCl, and triethylamine were added to a stirred solution of (5-(4-hydroxy-3-methoxyphenyl) thiazol-2-yl)(piperadin-1-yl)methanone hydrochloride and cinnoline-4-carboxylic acid in DCM. The reaction mixture was stirred at room temperature for 12 h. After completion of the reaction, solvent was distilled off, diluted with water, extracted and dried to afford Compound 11 as product.

$^1$H-NMR (300 MHz, DMSO-d$_6$) δ ppm 9.62 (s, 1H), 9.41 (s, 1H), 8.58 (d, J=7.8 Hz, 1H), 8.43 (s, 1H), 8.07-7.92 (m, 3H), 7.31 (d, J=2.1 Hz, 1H), 7.24 (dd, J=8.1, 2.1 Hz, 1H), 6.84 (d, J=8.4 Hz, 1H), 4.71-4.66 (m, 1H), 3.85 (s, 3H), 3.27-3.01 (m, 4H), 2.22-2.22 (m, 1H), 1.98-1.99 (m, 3H).

Example 3

Synthesis of Compound 20

The synthesis of 4,5-difluoro-pyridin-2-yl(2-(R)-(5-(3-fluoropyridin-2-yl)thiazol-2-carbonyl)-morpholin-4-yl) methanone (Compound 20 [FIG. 2B]) was a six-step process.

Potassium carbonate was added to (S)-morpholine-2-carboxylic acid dissolved in 1,4-dioxane-water and stirred for 30 minutes. Di-tert-butyl decarbonate was added and stirred at room temperature for 12 h. After completion of the reaction, solvent was distilled off. Crude was dissolved in water and acidified. Product was extracted as (S)-4-(tert-butoxycarbonyl) morpholine-2-carboxylic acid.

Carbonyldiimidazole in THF was added to a solution of (S)-4-(tert-butoxycarbonyl) morpholine-2-carboxylic acid in THF. The reaction mixture was stirred for 1 h. The mixture was cooled and a suspension of triethylamine and N,O-dimethylhydroxylamine in acetonitrile was added. The reaction was stirred for 16 h. Solvents were evaporated. The residue was dissolved in DCM and washed with water, acetic acid, and saturated sodium bicarbonate. Tert-butyl (S)-2-(((methoxy (methyl) amino) oxy) carbonyl) morpholine-4-carboxylate was isolated as product.

Potassium carbonate and 5-bromo-thiazole was added to a stirred solution of 2-(3-fluoropyridin-2-yl)-4,4,5,5-tetramethyl-1,3,2-dioxaborolane in 1,4-dioxane-water. The reaction mixture was de-gassed with nitrogen after which tetrakis(triphenylphosphine)palladium(0) was added. The reaction mixture was refluxed for 16 h. After completion of the reaction, the mixture diluted with water and extracted to afford 5-(3-fluoropyridin-2-yl) thiazole.

N-butyllithium in THF was added to a stirred solution of 5-(3-fluoropyridin-2-yl) thiazole in dry THF over 10 minutes. After 40 minutes, tert-butyl (S)-2-(((methoxy (methyl) amino) oxy) carbonyl) morpholine-4-carboxylate was added. The reaction mixture was stirred for 12 h. After completion of the reaction, the mixture was quenched in saturated ammonium chloride and extracted to afford tert-butyl (R)-2-(5-(3-fluoropyridin-2-yl) thiazole-2-carbonyl) morpholine-4-carboxylate.

2 M HCl in diethyl ether was added to a stirred solution of tert-butyl (R)-2-(5-(3-fluoropyridin-2-yl) thiazole-2-carbonyl) morpholine-4-carboxylate in DCM. The reaction mixture was stirred for 4 h. After completion of the reaction, solvent was distilled off to afford (R)-(5-(3-fluoropyridin-2-yl)thiazol-2-yl)(morpholin-2-yl)methanone hydrochloride.

Hydroxybenzotriazole, EDC-HCl, and triethylamine were added to a stirred solution of (R)-(5-(3-fluoropyridin-2-yl) thiazol-2-yl)(morpholin-2-yl)methanone hydrochloride and 4,5-difluoro-pyridine-2-carboxylic acid in DCM. The reaction mixture was allowed to stir for 12 h. After completion of the reaction, solvent was distilled off, diluted with water, extracted and dried to afford Compound 20 as product.

Example 4

Synthesis of Compound 34

The synthesis of 4,5-difluoro-pyridin-2-yl(2-(S)-(5-(3-fluoropyridin-2-yl)thiazol-2-carbonyl)-morpholin-4-yl) methanone (Compound 34 [FIG. 2C]) was a six-step process.

Potassium carbonate was added to (R)-morpholine-2-carboxylic acid dissolved in 1,4-dioxane-water and stirred for 30 minutes. Di-tert-butyl decarbonate was added and stirred at room temperature for 12 h. After completion of the reaction, solvent was distilled off. Crude was dissolved in water and acidified. Product was extracted as (R)-4-(tert-butoxycarbonyl) morpholine-2-carboxylic acid.

Carbonyldiimidazole in THF was added to a solution of (R)-4-(tert-butoxycarbonyl) morpholine-2-carboxylic acid in THF. The reaction mixture was stirred for 1 h. The mixture was cooled and a suspension of triethylamine and N,O-dimethylhydroxylamine in acetonitrile was added. The reaction was stirred for 16 h. Solvents were evaporated. The residue was dissolved in DCM and washed with water, acetic acid, and saturated sodium bicarbonate. Tert-butyl (R)-2-(((methoxy (methyl) amino) oxy) carbonyl) morpholine-4-carboxylate was isolated as product.

Potassium carbonate and 5-bromo-thiazole was added to a stirred solution of 2-(3-fluoropyridin-2-yl)-4,4,5,5-tetramethyl-1,3,2-dioxaborolane in 1,4-dioxane-water. The reaction mixture was de-gassed with nitrogen after which tetrakis(triphenylphosphine)palladium(0) was added. The reaction mixture was refluxed for 16 h. After completion of the reaction, the mixture diluted with water and extracted to afford 5-(3-fluoropyridin-2-yl) thiazole.

N-butyllithium in THF was added to a stirred solution of 5-(3-fluoropyridin-2-yl) thiazole in dry THF over 10 minutes. After 40 minutes, tert-butyl (R)-2-(((methoxy (methyl) amino) oxy) carbonyl) morpholine-4-carboxylate was added. The reaction mixture was stirred for 12 h. After completion of the reaction, the mixture was quenched in saturated ammonium chloride and extracted to afford tert-butyl (S)-2-(5-(3-fluoropyridin-2-yl) thiazole-2-carbonyl) morpholine-4-carboxylate.

2 M HCl in diethyl ether was added to a stirred solution of tert-butyl (S)-2-(5-(3-fluoropyridin-2-yl) thiazole-2-carbonyl) morpholine-4-carboxylate in DCM. The reaction mixture was stirred for 4 h. After completion of the reaction, solvent was distilled off to afford (S)-(5-(3-fluoropyridin-2-yl)thiazol-2-yl)(morpholin-2-yl)methanone hydrochloride.

Hydroxybenzotriazole, EDC-HCl, and triethylamine were added to a stirred solution of (S)-(5-(3-fluoropyridin-2-yl) thiazol-2-yl)(morpholin-2-yl)methanone hydrochloride and 4,5-difluoro-pyridine-2-carboxylic acid in DCM. The reaction mixture was allowed to stir for 12 h. After completion of the reaction, solvent was distilled off, diluted with water, extracted and dried to afford Compound 34 as product.

Example 5

Synthesis of Compound 40

The synthesis of 4-fluoro-pyridin-2-yl(2-(S)-(5-(3-fluoro-pyridin-2-yl)thiazol-2-carbonyl)-morpholin-4-yl)metha-none (Compound 40 [FIG. 2D]) was a six-step process.

(S)-(5-(3-fluoropyridin-2-yl)thiazol-2-yl)(morpholin-2-yl)methanone hydrochloride was produced as described in Example 4. Hydroxybenzotriazole, EDC-HCl, and triethyl-amine were added to a stirred solution of (S)-(5-(3-fluoro-pyridin-2-yl)thiazol-2-yl)(morpholin-2-yl)methanone hydrochloride and 4-fluoro-pyridine-2-carboxylic acid in DCM. The reaction mixture was allowed to stir for 12 h. After completion of the reaction, solvent was distilled off, diluted with water, extracted and dried to afford Compound 40 as product.

Example 6

Synthesis of Compound 37

Figures 2E, 2F, 2G, 2H:
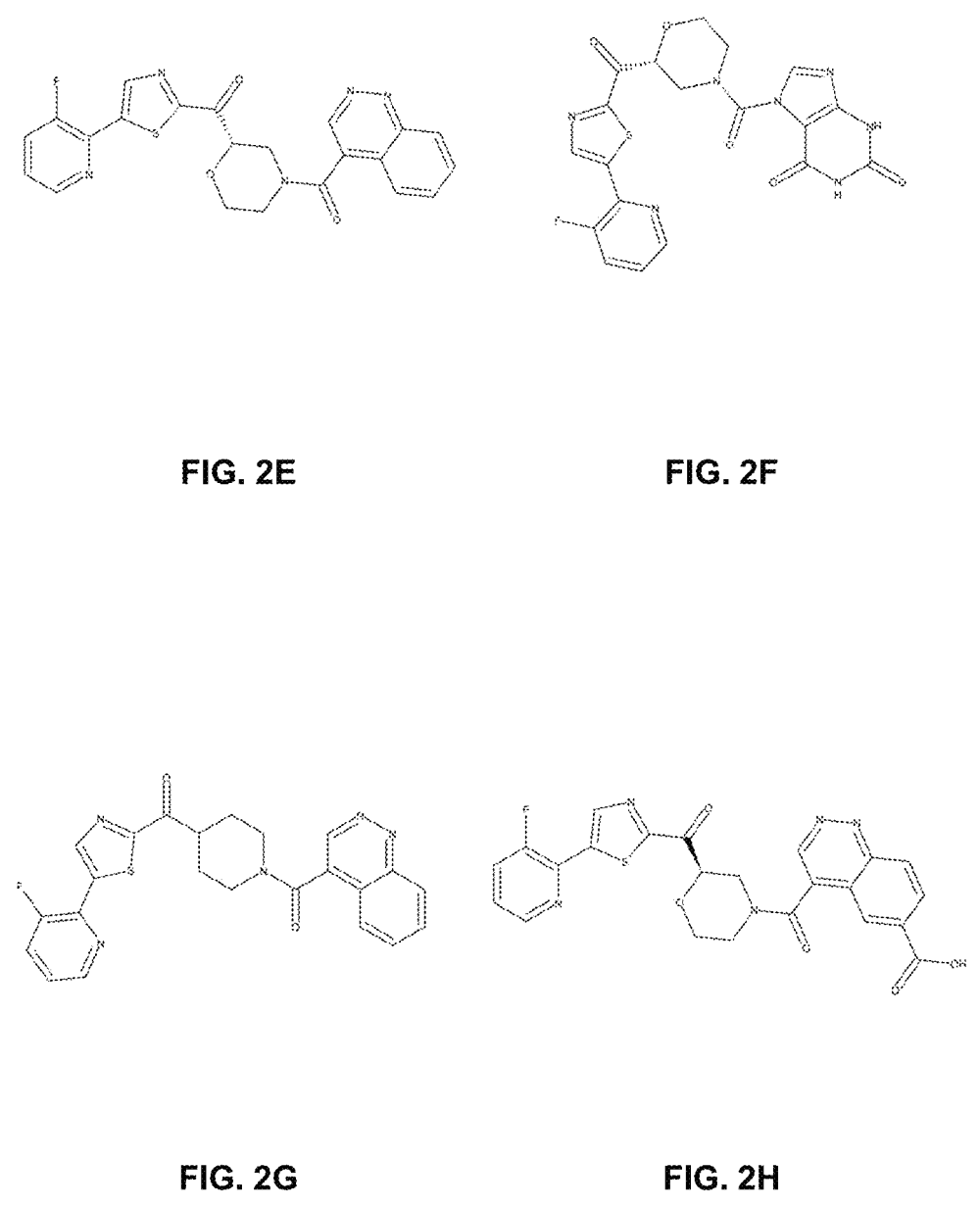

The synthesis of cinnolin-4-yl(2-(S)-(5-(3-fluoropyridin-2-yl)thiazol-2-carbonyl)-morpholin-4-yl)methanone (Compound 37 [FIG. 2E]) was a six-step process.

(S)-(5-(3-fluoropyridin-2-yl)thiazol-2-yl)(morpholin-2-yl)methanone hydrochloride was produced as described in Example 4. Hydroxybenzotriazole, EDC-HCl, and triethyl-amine were added to a stirred solution of (S)-(5-(3-fluoro-pyridin-2-yl)thiazol-2-yl)(morpholin-2-yl)methanone hydrochloride and cinnoline-4-carboxylic acid in DCM. The reaction mixture was allowed to stir for 12 h. After completion of the reaction, solvent was distilled off, diluted with water, extracted and dried to afford Compound 37 as product.

Example 7

Synthesis of Compound 42

The synthesis of 3H-purine-2,6-dion-7-yl(2-(S)-(5-(3-fluoropyridin-2-yl)thiazol-2-carbonyl)-morpholin-4-yl) methanone (Compound 42 [FIG. 2F]) was a seven-step process.

(S)-(5-(3-fluoropyridin-2-yl)thiazol-2-yl)(morpholin-2-yl)methanone hydrochloride was produced as described in Example 4. Triphosgene and triethylamine were added to a stirred solution of (S)-(5-(3-fluoropyridin-2-yl)thiazol-2-yl)(morpholin-2-yl)methanone hydrochloride and 2,6-dichloropurine. The reaction mixture was allowed to stir for 12 h. After completion of the reaction, solvent was distilled off, diluted with water, extracted to afford 3H-2,6-dichloropurine-7-yl(2-(S)-(5-(3-fluoropyridin-2-yl)thiazol-2-carbonyl)-morpholin-4-yl)methanone.

Sodium acetate was added to a stirred solution of 3H-2,6-dichloropurine-7-yl(2-(S)-(5-(3-fluoropyridin-2-yl)thiazol-2-carbonyl)-morpholin-4-yl)methanone. The reaction was stirred for 12 hours. After completion of the reaction, solvent was distilled off, diluted with water, extracted to afford Compound 42 as product.

Example 8

Synthesis of Compound 52

The synthesis of cinnolin-4-yl(4-(5-(3-fluoropyridin-2-yl) thiazole-2-carbonyl)-piperidin-1-yl)methanone (Compound 52 [FIG. 2G]) was a five-step process.

Carbonyldiimidazole was added to a solution of 1-(tert-butoxycarbonyl) piperidine-4-carboxylic acid in DCM. After 40 minutes, N,O-dimethylhydroxylamine hydrochloride was added to the reaction mixture. The reaction mixture was stirred at room temperature for 12 h. After completion of the reaction, the reaction mixture was diluted with cold water. Tert-butyl 4-(methoxy(methyl)carbamoyl)piperidine-1-carboxylate was isolated as product.

Potassium carbonate and 5-bromo-thiazole was added to a stirred solution of 2-(3-fluoropyridin-2-yl)-4,4,5,5-tetramethyl-1,3,2-dioxaborolane in 1,4-dioxane-water. The reaction mixture was de-gassed with nitrogen after which tetrakis(triphenylphosphine)palladium(0) was added. The reaction mixture was refluxed for 16 h. After completion of the reaction, the mixture diluted with water and extracted to afford 5-(3-fluoropyridin-2-yl) thiazole.

N-butyllithium was added to a stirred solution of 5-(3-fluoropyridin-2-yl) thiazole in dry THF over 10 minutes. After 40 minutes, tert-butyl 4-(methoxy(methyl)carbamoyl) piperidine-1-carboxylate dissolved in dry THF was added. The reaction mixture was stirred for 12 h. After completion of the reaction, the mixture was quenched in saturated ammonium chloride, extracted and dried to afford tert-butyl 4-(5-(3-fluoropyridin-2-yl)thiazole-2-carbonyl) piperidine-1-carboxylate as product.

Ether (2 M) in hydrochloric acid was added to a stirred solution of tert-butyl 4-(5-(3-fluoropyridin-2-yl) thiazole-2-carbonyl) piperidine-1-carboxylate in DCM. The reaction mixture was stirred at room temperature for 12 h. After completion of the reaction, solvent was distilled off to afford (5-(3-fluoropyridin-2-yl) thiazol-2-yl)(piperidin-4-yl) methanone hydrochloride as product.

Hydroxybenzotriazole, EDC-HCl, and triethylamine were added to a stirred solution of (5-(3-fluoropyridin-2-yl) thiazol-2-yl)(piperadin-1-yl)methanone hydrochloride and cinnoline-4-carboxylic acid in DCM. The reaction mixture was stirred at room temperature for 12 h. After completion of the reaction, solvent was distilled off, diluted with water, extracted and dried to afford Compound 52 as product.

Example 9

Synthesis of Compound 68

The synthesis of 6-carboxycinnolin-4-yl(2-(R)-(5-(3-fluoropyridin-2-yl)thiazol-2-carbonyl)-morpholin-4-yl) methanone (Compound 68 [FIG. 2H]) was a six-step process.

(R)-(5-(3-fluoropyridin-2-yl)thiazol-2-yl)(morpholin-2-yl)methanone hydrochloride was produced as described in Example 3. Hydroxybenzotriazole, EDC-HCl, and triethylamine were added to a stirred solution of (R)-(5-(3-fluoropyridin-2-yl)thiazol-2-yl)(morpholin-2-yl)methanone hydrochloride and 6-methylcinnoline-4-carboxylic acid in DCM. The reaction mixture was allowed to stir for 12 h. After completion of the reaction, solvent was distilled off, diluted with water, extracted and dried to afford 6-methyl-cinnolin-4-yl(2-(R)-(5-(3-fluoropyridin-2-yl)thiazol-2-carbonyl)-morpholin-4-yl)methanone.

Potassium permanganate was added to a stirred solution of 6-methylcinnolin-4-yl(2-(R)-(5-(3-fluoropyridin-2-yl) thiazol-2-carbonyl)-morpholin-4-yl)methanone. The reaction mixture was stirred followed by the addition of hydrochloric acid. After completion of the reaction, the mixture was diluted with water, extracted and dried to afford Compound 68 as product.

Example 10

Synthesis of Compound 6

The synthesis of 4-fluoro-5-methoxy-pyridin-2-yl(2-(S)-(5-(3-fluoropyridin-2-yl)thiazol-2-carbonyl)-morpholin-4-yl)methanone (Compound 6 [FIG. 2I]) was a six-step process.

(S)-(5-(3-fluoropyridin-2-yl)thiazol-2-yl)(morpholin-2-yl)methanone hydrochloride was produced as described in Example 4. Hydroxybenzotriazole, EDC-HCl, and triethylamine were added to a stirred solution of (S)-(5-(3-fluoropyridin-2-yl)thiazol-2-yl)(morpholin-2-yl)methanone hydrochloride and 4-fluoro-5-methoxy-pyridine-2-carboxylic acid in DCM. The reaction mixture was allowed to stir for 12 h. After completion of the reaction, solvent was distilled off, diluted with water, extracted and dried to afford Compound 6 as product.

Example 11

Synthesis of Compound 7

The synthesis of 4-fluoro-5-methoxy-pyridin-2-yl(2-(R)-(5-(3-fluoropyridin-2-yl)thiazol-2-carbonyl)-morpholin-4-yl)methanone (Compound 7 [FIG. 2J]) was a six-step process.

(R)-(5-(3-fluoropyridin-2-yl)thiazol-2-yl)(morpholin-2-yl)methanone hydrochloride was produced as described in Example 3. Hydroxybenzotriazole, EDC-HCl, and triethylamine were added to a stirred solution of (R)-(5-(3-fluoro-pyridin-2-yl)thiazol-2-yl)(morpholin-2-yl)methanone hydrochloride and 4-fluoro-5-methoxy-pyridine-2-carboxylic acid in DCM. The reaction mixture was allowed to stir for 12 h. After completion of the reaction, solvent was distilled off, diluted with water, extracted and dried to afford Compound 7 as product.

Example 12

Synthesis of Compound 55

The synthesis of 4-fluoro-pyridin-2-yl(4-(5-(3-fluoropyridin-2-yl)thiazole-2-carbonyl)-piperidin-1-yl)methanone (Compound 55 [FIG. 2K]) was a five-step process.

(5-(3-fluoropyridin-2-yl) thiazol-2-yl)(piperidin-4-yl) methanone hydrochloride was produced as described in Example 8. Hydroxybenzotriazole, EDC-HCl, and triethylamine were added to a stirred solution of (5-(3-fluoropyridin-2-yl) thiazol-2-yl)(piperadin-1-yl)methanone hydrochloride and 4-fluoropyridine-2-carboxylic acid in DCM. The reaction mixture was stirred at room temperature for 12 h. After completion of the reaction, solvent was distilled off, diluted with water, extracted and dried to afford Compound 55 as product.

Example 13

Synthesis of Compound 58

The synthesis of 4,5-difluoro-pyridin-2-yl(4-(5-(3-fluoro-pyridin-2-yl)thiazole-2-carbonyl)-piperazin-1-yl)methanone (Compound 58 [FIG. 2L]) was a five-step process.

Potassium carbonate was added to a stirred solution of 2-(3-fluoropyridin-2-yl)-4,4,5,5-tetramethyl-1,3,2-dioxaborolane and methyl 5-bromothiazole-2-carboxylate in 1,4-dioxane-water. The reaction mixture was de-gassed with nitrogen after which tetrakis(triphenylphosphine)palladium (0) was added. The reaction mixture was stirred for 12 h. After completion of the reaction, the mixture diluted with water and extracted to afford methyl 5-(3-fluoropyridin-2-yl) thiazole-2-carboxylate.

Lithium hydroxide in water was added to a stirred solution of methyl 5-(3-fluoropyridin-2-yl) thiazole-2-carboxylate. The reaction mixture stirred for 12 h. After completion of the reaction, the mixture was diluted with water, acidified with 1N HCl solution, and precipitated to afford 5-(3-fluoropyridin-2-yl) thiazole-2-carboxylic acid.

N,N-Diisopropylethylamine and HATU were added to a stirred solution of 5-(3-fluoropyridin-2-yl) thiazole-2-carboxylic acid and tert-butyl piperazine-1-carboxylate in DMF. The reaction mixture was stirred for 12 h. After completion of the reaction, solvent was distilled off. The residue was diluted with water and extracted to afford tert-butyl 4-(5-(3-fluoropyridin-2-yl)) thiazole-2-carbonyl) piperazine-1-carboxylate.

Ether in hydrochloric acid was added to a stirred solution of tert-butyl 4-(5-(3-fluoropyridin-2-yl)) thiazole-2-carbonyl) piperazine-1-carboxylate in DCM. The reaction mixture was stirred for 12 h. After completion of the reaction, solvent was distilled off to afford (5-(3-fluoropyridin-2-yl) thiazol-2-yl)(piperazin-1-yl)methanone hydrochloride.

N,N-Diisopropylethylamine and HATU were added to a stirred solution of (5-(3-fluoropyridin-2-yl) thiazol-2-yl) (piperazin-1-yl)methanone hydrochloride and 4,5-difluoro-pyridine-2-carboxylic acid in DMF. The reaction mixture was stirred for 12 h. After completion of the reaction, solvent was distilled off, diluted with water, extracted and dried to afford Compound 58 as product.

Example 14

Synthesis of Compound 69

The synthesis of 2-((S)-2-(5-(2-fluorophenyl) thiazole-2-carbonyl) morpholine-4-carbonyl)-4a,7-dihydropyrrolo[1,2-b]pyridazin-4(1H)-one (Compound 69 [FIG. 2M]) was a six-step process.

Potassium carbonate was added to (R)-morpholine-2-carboxylic acid dissolved in 1,4-dioxane-water and stirred for 30 minutes. Di-tert-butyl decarbonate was added and stirred at room temperature for 12 h. After completion of the reaction, solvent was distilled off. Crude was dissolved in water and acidified. Product was extracted as (R)-4-(tert-butoxycarbonyl) morpholine-2-carboxylic acid.

Carbonyldiimidazole in THF was added to a solution of (R)-4-(tert-butoxycarbonyl) morpholine-2-carboxylic acid in THF. The reaction mixture was stirred for 1 h. The mixture was cooled and a suspension of triethylamine and N,O-dimethylhydroxylamine in acetonitrile was added. The reaction was stirred for 16 h. Solvents were evaporated. The residue was dissolved in DCM and washed with water, acetic acid, and saturated sodium bicarbonate. Tert-butyl (R)-2-(((methoxy (methyl) amino) oxy) carbonyl) morpholine-4-carboxylate was isolated as product.

Potassium carbonate and 5-bromo-thiazole was added to a stirred solution of 2-(2-fluorophenyl)-4,4,5,5-tetramethyl-1,3,2-dioxaborolane in 1,4-dioxane-water. The reaction mixture was de-gassed with nitrogen after which tetrakis(triphenylphosphine)palladium(0) was added. The reaction mixture was refluxed for 16 h. After completion of the reaction, the mixture diluted with water and extracted to afford 5-(2-fluorophenyl) thiazole.

N-butyllithium in THF was added to a stirred solution of 5-(2-fluorophenyl) thiazole in dry THF over 10 minutes. After 40 minutes, tert-butyl (R)-2-(((methoxy (methyl) amino) oxy) carbonyl) morpholine-4-carboxylate was added. The reaction mixture was stirred for 12 h. After completion of the reaction, the mixture was quenched in saturated ammonium chloride and extracted to afford tert-butyl (S)-2-(5-(2-fluorophenyl) thiazole-2-carbonyl) morpholine-4-carboxylate.

2 M HCl in diethyl ether was added to a stirred solution of tert-butyl (S)-2-(5-(2-fluorophenyl) thiazole-2-carbonyl) morpholine-4-carboxylate in DCM. The reaction mixture was stirred for 4 h. After completion of the reaction, solvent was distilled off to afford (S)-(5-(2-fluorophenyl)thiazol-2-yl)(morpholin-2-yl)methanone hydrochloride.

Hydroxybenzotriazole, EDC-HCl, and triethylamine were added to a stirred solution of (S)-(5-(2-fluorophenyl)thiazol-2-yl)(morpholin-2-yl)methanone hydrochloride and 4-oxo-1,4-dihydropyrrolo[1,2-b]pyridazine-2-carboxylic acid in DCM. The reaction mixture was allowed to stir for 12 h. After completion of the reaction, solvent was distilled off, diluted with water, extracted and dried to afford Compound 69 as product.

Example 15

CD4+ T Cell Responses

Introduction

CD4+ T cells are central to the generation of inflammation in a variety of conductions. In addition, CD4+ T cells are primary responders to the IL-18 cytokine. As such, CD4+ T cells were cultured in vitro in the presence of selected compounds to test for pharmacological activity.

Methods

CD4+ T cell culture. Spleens were excised from mice and crushed between frosted microscope slides. Cellular suspension was filtered, centrifuged and exposed to hypotonic lysis to remove red blood cells. CD4+ T cells were enriched by magnetic sorting. Cells were re-suspended in IMDM and cultured in CD3- and CD28-coated round bottom wells. Cells were treated with indicated compounds at 10 and 100 nM or vehicle for 24 hours. During the final 6 hours, cells were stimulated with phorbol myristate acetate and ionomycin. Cells were then collected and stained with antibodies to detect CD45+ CD4+ IFNγ+ cells by flow cytometry. Data was acquired using a FACS Celesta flow cytometer with FACSDiva software.

Results

Compounds 11, 34, 37, 40 and 69 significantly reduced the proportion of CD4+ IFNγ+ cells at the 100 nM concentration relative to vehicle treated wells (FIG. 3). In addition, compounds 11, 34, and 40 significantly reduced these cells at a concentration of 10 nM.

Example 16

DSS Colitis

Introduction

Inflammation of the gastrointestinal tract can be caused by numerous factors including food antigens, infectious agents, autoimmunity, or radiation. The dextran sulfate sodium (DSS) model provides a model system where the epithelial barrier is disrupted in the distal intestine allowing for translocation of bacteria and generation of immune responses.

Methods

DSS model. Mice were given DSS in drinking water for seven days. At project initiation, mice were approximately 8 weeks of age and began dosing 24 hours after being placed on DSS water. Treatments were prepared within a 0.5% methylcellulose solution. The dosage used was 20 mg/kg delivered once daily. At conclusion, colons were scored macroscopically for presence of lesions, blood, stool consistency, mucosal thickening, friability and length on a summarized score from 0 to 4.

Flow cytometry. Colons were collected into RPMI/FBS buffer containing collagenase and DNase for digestion. Tissues were digested for 60 minutes under stifling at 37° C. Resultant cellular suspensions were filtered through 100 um strainers, centrifuged and washed in fresh RPMI. Following filtration, immune cells were purified by Percoll gradient of the cell-containing 40% Percoll overlayed onto 70% Percoll solution. After centrifugation, interphase was collected and washed to obtain enriched colonic lamina propria cell fractions. Cells were labeled with mixtures of extracellular and intracellular antibodies to quantify the presence of CD45+ CD3+ CD4+ CD8- IFNγ+ cells. Data was acquired using a FACS Celesta flow cytometer with FACSDiva software.

Results

Figure 4A:
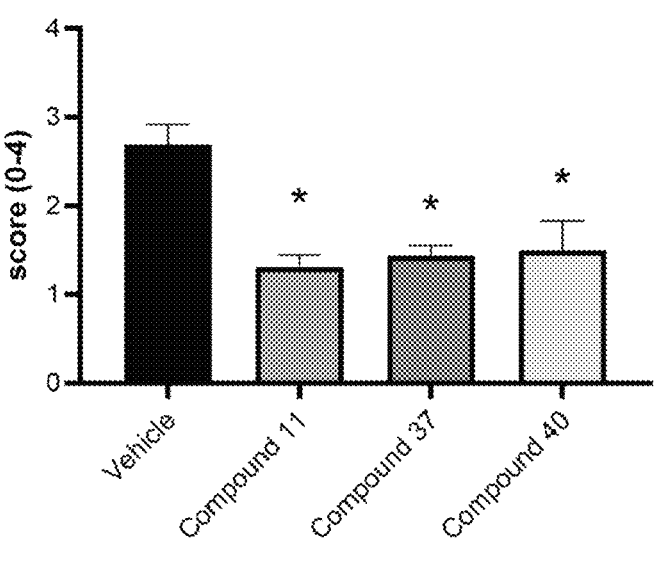
FIGS. 4A and 4B are graphs providing experimental validation of in vivo pharmacological action of three exemplary compounds in a DSS colitis model. Measurements are of disease severity by macroscopic colon score (FIG. 4A) and colonic lamina propria CD4+ IFNγ+ cells by flow cytometry (FIG. 4B).
Figure 4B:
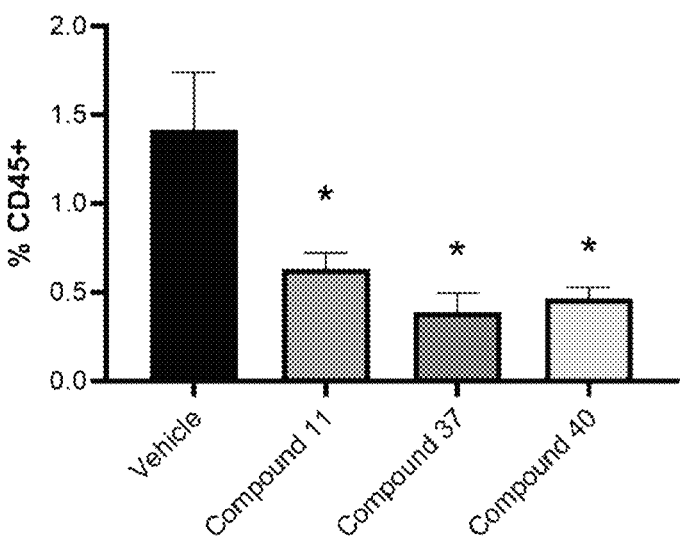

Oral treatment with compounds 11, 37 and 40 reduced the severity of disease by macroscopic scoring of the colon (FIG. 4A) relative to the group receiving vehicle only. Each of these three compounds reducing the proportion of CD4+ IFNγ+ cells in the colonic lamina propria (FIG. 4B).

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A compound selected from the group consisting of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, and 69 as follows:

-continued

21
-continued

22
-continued

10

16

11

17

15

20

18

12

30

19

13

40

35

14

20

50

55

15

21

60

22

65

23

-continued

24

-continued

25

-continued

28

29

30

31

32

41

26

-continued

42

43

44

45

46

47

-continued

-continued

48

49

50

51

52

53

54

55

56

57

58

59

29

-continued

30

-continued

2. The compound of claim 1, wherein the compound is selected from the group consisting of compounds 6, 7, 11, 20, 34, 37, 40, 42, 52, 55, 58, 68 and 69.

3. The compound of claim 1, wherein the compound is selected from the group consisting of compounds 11, 37 and 40.

4. The compound of claim 1, wherein the compound is compound 11.

5. A method of treating a disease characterized by excess CD4+ IFNγ+ cells in a patient, the method comprising administering the compound of claim 1 to the patient in a manner sufficient to treat the disease.

* * * * *